US006432646B1

(12) United States Patent
Gasser et al.

(10) Patent No.: US 6,432,646 B1
(45) Date of Patent: Aug. 13, 2002

(54) PCR-BASED IDENTIFICATION OF EIMERIA SPECIES AND STRAINS

(75) Inventors: Robin Beat Gasser, Werribee; Wayne Geoffrey Woods, Sunbury; David Grant Richards, Frankston North; Kevin George Whithear, Port Melbourne, all of (AU)

(73) Assignee: The University of Melbourne, Victoria (AU)

( * ) Notice: Subject to any disclaimer, the term of this patent is extended or adjusted under 35 U.S.C. 154(b) by 0 days.

(21) Appl. No.: 09/527,223

(22) Filed: Mar. 16, 2000

(51) Int. Cl.[7] .......................... C12Q 1/68; C12P 19/34; C07H 21/04; G01N 21/00
(52) U.S. Cl. ...................... 435/6; 435/91.2; 536/24.32; 536/24.33; 356/344
(58) Field of Search .......................... 435/6, 91.1, 91.2; 536/24.33, 24.3, 24.31, 24.32; 356/344

(56) References Cited

U.S. PATENT DOCUMENTS 5,770,368 A * 6/1998 De Leon et al. ................. 435/6

FOREIGN PATENT DOCUMENTS

| AU | 17250/92 | 12/1992 |
| EP | 516381 A2 | 2/1992 |

OTHER PUBLICATIONS

Fernandez, S. et al. Memorial do Instituto Oswaldo Cruz 94(Suppl II):MB–80 (Nov. 1999).*
Gasser et al. Sequence–based analysis of enzymatically amplified DNA fragments by mutation detection techniques. Parasitology Today, vol. 15, No. 11, Nov. 1999.*
Schnitzler et al. PCR identification of Chicken Eimeria: A simplified read-out. Avian Pathology, vol. 28, pp. 89–93, Feb. 1999.*
Barta et al. Genbank Accession No. AFO27722, submitted Dec. 2, 1997.*
Woods et al, *International J. for Parasitology*, 30:1019–1023 (2000).
EMBL Database Accession No. AF026388, *Eimeria tenella* small subunit ribosomal RNA 5.8S ribosomal RNA, and large submit ribosomal RNA genes, and internal transcribed spacer 1 and 2, (Nov. 5, 1997).
EMBL Database Accession No. AF065094, *Eimeria maxima* internal transcribed spacer 1 (Dec. 29, 1998).
Shirley et al, *Guidelines on Techniques in Coccidiosis Research*, European Commission, Luxembourg, pp. 1–24 (1995).
Gasser et al, *Parasatology Today*, 15:462 (1999).
Tsuji et al, *J. of Parisitology*, 83(5):966–970 (1997).
Andrews et al, *Int. J. Parasitol.*, 29:213–253 (1999).
Barta et al, *J. Parasitol.*, 83:262–271 (1997).
Barta et al, *Int. J. Parasitol.*, 28:485–492 (1998).
Eckert et al, *Guidelines on Techniques in Coccidiosis Research*, European Commission, Luexembourg, pp. 103–119 (1995).
Ellsworth et al, *Biotechniques*, 14:214–217 (1993).
Gasser et al, *Parasitol. Res.*, 74:103–111 (1987).
Gasser et al, *Int. J. Parasitol.*, 27:1449–1463 (1997).
Greif et al, *Parasitol. Res.*, 82:706–714 (1996).
Johnston et al, *Parasitol. Res.*, 81:91–97 (1995).
Johnston et al, *Parasitol. Res.*, 83:464–470 (1997).
MacPherson et al, *Mol. Cell. Probes*, 7:293–299 (1993).
McDougald et al, *Diseases of Poultry*, 10th Ed., Iowa State University Press, Ames, Iowa, pp. 865–883 (1997).

(List continued on next page.)

*Primary Examiner*—Carla J. Myers
*Assistant Examiner*—Diana Johannsen
(74) *Attorney, Agent, or Firm*—Sughrue Mion, PLLC

(57) ABSTRACT

A PCR-based method for the identification of species of the genus Eimeria, (commonly known as coccidia), is described. The method is genus-specific and utilizes either, or both, of two novel primer sets; designated WW1 (SEQ ID NO:31) and WW3r (SEQ ID NO:32), and, WW2 (SEQ ID NO:33) and WW4r (SEQ ID NO:34).

9 Claims, 5 Drawing Sheets

OTHER PUBLICATIONS

Molloy et al, *Avian Dis.*, 42:119–123 (1998).
Orita et al, *Genomics*, 5:874–879 (1989).
Sambrook et al, *Molecular Cloning: A Laboratory Manual*, 2nd Ed., Cold Spring Harbour Press (1989).
Schnitzler et al, *Avian Pathol.*, 27:490–497 (1998).
Schnitzler et al, *Avian Pathol.*, 28:89–93 (1999).
Shirley et al, *Parasitol. Res.*, 80:346–351 (1994).
Shirley et al, *Res. Vet. Sci.*, 57:10–14 (1994).
Stucki et al, *Exp. Parasitol.*, 76:68–75 (1993).
Zhu et al, *Electrophoresis*, 19:1366–1373 (1998).

* cited by examiner

FIG. 1

WW1-TCTAAAGGATGCAAAAGTCGTAACACGGTTTCCGTAGTGAACCTGCGGAAGGATCATTCACACAATTCGCACGCCT
GGAACGCGCTGCTGGTTTACAGGTTTCAAGCATTCGCTTGCCTGGGTGGCCAGCAGGTAGTCGTCGGTGTTGTTG
GAAAGAAAACTTTAGTCGCAACCCTGAATCTGTTTTCTGCAACGTTTTCTACTTTTTAAAAATTGAAGGA
ATTTTTGCTGCTGCAAGGATATATCGCAGTAGTATGTACGTGGGGCGGATCGGGGGGGTGGTGGCGCATGCACGGCTCGC
GTGGGGCCTGTCGGTGGCAGCCAGCGCCCAGCCCCGTGATCGTCGGCTCGATCGCGCCACGTACGTGGAGGGATTAT
GAGAGGAGAAGACGCGCACGGGCGTCTGTCGTTCCGTTACATGCTGCTTGAACTTGCTTGCTTCAGCAAGAAACCTTT
CTGCATGCTGGTGCTGCGTGTGAATCGAATCACTTTTGTTGATGAGCAGAAGGAAGAATAGGTAGAAATCGGAAAAAAC-WW3R
GCTCACTAAGTGTGAATCGAATCACTTTTGTTGATGAGCAGAAGGAAGAATAGGTAGAAATCGGAAAAAAC-WW3R

FIG. 2

WW2-CTTAACAACTCCTACTAGTAGGCCATGCTGCTGCTGCTGTCTCTGTTCCTTGTTGGTCCTGTGAGGGTTCGGCGATGCT
GCCGACAGAAGTGAGTGCTTTGCTGCTCGTTTGTGCTGCGGAATTTTTCGGGTCACCAAAGGGGAGGTAGAAGCAT
GTTTGGTTTCATTTGAGTGTCGTTGCATTGGTTTTGAAGGAGATGCGGCGTCTCGAAATTGTTGTCCAGCCGGTGCTG
TGTGTCTGCACAGTGTGCCGTTTTCCATGCCGTGCTTTCGTGCTCCTTCATTCGGAAAGAGAGAG
ATACGGTGGTTGTATTTTATGCAACGTGTTGTCCGTTCTGGACGAATGTTTTGAGCAGGGCTAGGGCGAGGTATAATA
GTGCATGGGTATGCGACAACGTGAAACGACATATAGTACACGGCACCATGGACGTGTTGCATGCGTGCTTTTTCGGTA
TTAACACATGTATGTATAGACCTGAAATCAGT-WW4R

ITS-1

ITS-2

SEQUENCE LISTING

<160> NUMBER OF SEQ ID NOS: 34

<210> SEQ ID NO 1
<211> LENGTH: 626
<212> TYPE: DNA
<213> ORGANISM: Eimeria tenella -continued

```
<400> SEQUENCE: 1
tctaaaggat gcaaaagtcg taacacggtt tccgtagtga acctgcggaa ggatcattca      60
cacaattcgc acgcctggaa cgcgctgctg gttttacagg tttcaagcat tcgctttgcc     120
tgggtggcca gcagcaggta gtcgtcggtg ttgttggaaa gaaaacttta gtccatcgca     180
acccttgaat ctgttttttct ctgcaacggt ttttctactt tttaaaaatt gaaggaattt    240
tttgctgctg caaggatata tcgcagtagt atgtacgtgg gcgatcgggg gggtggtggc     300
gcatgcacgg gctcgcgtgg ggcctgtcgg tggcagcccc agcgcgccgg cgcagccccg     360
tgatcgtcga tcgcgcacgt acgtggaggg gattatgaga ggagaagacg cgcacggggc     420
tgtgtcgtat gcagagcgct cgcggctcgg gcgattgttc cgtgttgtgt gctctgctgc     480
atgctggtgt gtgcgttctg tctctctctc tctccgttac atgctgcttg aactttgct     540 tcagcaagaa acctttgctc actaaggtga atcgaatcac ttttgttgat gagcagaagg     600
aagaataggt agaaatcgga aaaaac                                         626

<210> SEQ ID NO 2
<211> LENGTH: 512
<212> TYPE: DNA
<213> ORGANISM: Eimeria tenella

<400> SEQUENCE: 2
cttaacaact cctactagta ggccatgctg ctgtctgtct ctgttccttg tggtcctgtg      60
agggttcggc gatgctgccg acagaagtga gtgctttgct cgtttctgtt ttgtgtcgcg     120
gaattttttc gggtcaccaa aggggaggta gaagcatgtt tggtttcatt tgagtgtcgt     180
tgcattggtt ttgaaggaga tgcggcgtct ctcgaaattg ttgtcggcag cggtgctgtg     240
tgtctgcaca gtgtgccgtt ttccatgcct gtgctttcta tagtgtcgtc gtatgctcct     300
ttcattcgga aagagagaga tacggtggtt gtattttatg caacgttgtt tgtctcgttc     360
tggacgaatg ttttgagcag ggctagggcg aggtataata gtgcatgggt atgcgacaac     420
gtgaaacgac atatagtaca cggcaccatg gacgtgttgc atgcgtcgtt ttttttcggt     480
attacacatg tatgtataga cctgaaatca gt                                  512

<210> SEQ ID NO 3
<211> LENGTH: 10
<212> TYPE: DNA
<213> ORGANISM: synthetic construct

<400> SEQUENCE: 3
tctaaaggat                                                            10

<210> SEQ ID NO 4
<211> LENGTH: 4
<212> TYPE: DNA
<213> ORGANISM: synthetic construct

<400> SEQUENCE: 4 cagc                                                                   4

<210> SEQ ID NO 5
<211> LENGTH: 5
<212> TYPE: DNA
<213> ORGANISM: synthetic construct

<400> SEQUENCE: 5
``` gttttt                                                                    5

<210> SEQ ID NO 6
<211> LENGTH: 10
<212> TYPE: DNA
<213> ORGANISM: synthetic construct

<400> SEQUENCE: 6
atgcgtgagc                                                               10

<210> SEQ ID NO 7
<211> LENGTH: 10
<212> TYPE: DNA
<213> ORGANISM: synthetic construct

<400> SEQUENCE: 7
actgatttca                                                               10

<210> SEQ ID NO 8
<211> LENGTH: 10
<212> TYPE: DNA
<213> ORGANISM: synthetic construct

<400> SEQUENCE: 8
tgatatgctt                                                               10

<210> SEQ ID NO 9
<211> LENGTH: 19
<212> TYPE: DNA
<213> ORGANISM: synthetic construct

<400> SEQUENCE: 9
agttgcgtaa atagagccc                                                     19

<210> SEQ ID NO 10
<211> LENGTH: 19
<212> TYPE: DNA
<213> ORGANISM: synthetic construct

<400> SEQUENCE: 10
aagacatcca ttgctgaaa                                                     19

<210> SEQ ID NO 11
<211> LENGTH: 18
<212> TYPE: DNA
<213> ORGANISM: synthetic construct

<400> SEQUENCE: 11
aagttgcgta aaagagcc                                                      18

<210> SEQ ID NO 12
<211> LENGTH: 19
<212> TYPE: DNA
<213> ORGANISM: synthetic construct

<400> SEQUENCE: 12
caagacatcc attgctgaa                                                     19

<210> SEQ ID NO 13
<211> LENGTH: 18
<212> TYPE: DNA
<213> ORGANISM: synthetic construct

<400> SEQUENCE: 13

```
aagttgcgta aatagagc                                              18

<210> SEQ ID NO 14
<211> LENGTH: 18
<212> TYPE: DNA
<213> ORGANISM: synthetic construct

<400> SEQUENCE: 14
caagacatcc attgctga                                              18

<210> SEQ ID NO 15
<211> LENGTH: 17
<212> TYPE: DNA
<213> ORGANISM: synthetic construct

<400> SEQUENCE: 15
ttgcgtaaat agagccc                                               17

<210> SEQ ID NO 16
<211> LENGTH: 17
<212> TYPE: DNA
<213> ORGANISM: synthetic construct

<400> SEQUENCE: 16
gacatccatt gctgaaa                                               17

<210> SEQ ID NO 17
<211> LENGTH: 17
<212> TYPE: DNA
<213> ORGANISM: synthetic construct

<400> SEQUENCE: 17
cgtctgtttc agtgtct                                               17

<210> SEQ ID NO 18
<211> LENGTH: 19
<212> TYPE: DNA
<213> ORGANISM: synthetic construct

<400> SEQUENCE: 18
aattcagcgg gtaacctcg                                             19

<210> SEQ ID NO 19
<211> LENGTH: 17
<212> TYPE: DNA
<213> ORGANISM: synthetic construct

<400> SEQUENCE: 19
acgtctgttt cagtgtc                                               17

<210> SEQ ID NO 20
<211> LENGTH: 19
<212> TYPE: DNA
<213> ORGANISM: synthetic construct

<400> SEQUENCE: 20
aaattcagcg ggtaacctc                                             19

<210> SEQ ID NO 21
<211> LENGTH: 17
<212> TYPE: DNA
<213> ORGANISM: synthetic construct
```

-continued

```
<210> SEQ ID NO 22
<211> LENGTH: 18
<212> TYPE: DNA
<213> ORGANISM: synthetic construct

<400> SEQUENCE: 22
aaattcagcg ggtaacct                                              18

<210> SEQ ID NO 23
<211> LENGTH: 16
<212> TYPE: DNA
<213> ORGANISM: synthetic construct

<400> SEQUENCE: 23
gtctgtttca gtgtct                                                16

<210> SEQ ID NO 24
<211> LENGTH: 17
<212> TYPE: DNA
<213> ORGANISM: synthetic construct

<400> SEQUENCE: 24
ttcagcgggt aacctcg                                               17

<210> SEQ ID NO 25
<211> LENGTH: 20
<212> TYPE: DNA
<213> ORGANISM: synthetic construct

<400> SEQUENCE: 25
aagttgcgta aatagagccc                                            20

<210> SEQ ID NO 26
<211> LENGTH: 20
<212> TYPE: DNA
<213> ORGANISM: synthetic construct

<400> SEQUENCE: 26
caagacatcc attgctgaaa                                            20

<210> SEQ ID NO 27
<211> LENGTH: 18
<212> TYPE: DNA
<213> ORGANISM: synthetic construct

<400> SEQUENCE: 27
acgtctgttt cagtgtct                                              18

<210> SEQ ID NO 28
<211> LENGTH: 20
<212> TYPE: DNA
<213> ORGANISM: synthetic construct

<400> SEQUENCE: 28
aaattcagcg ggtaacctcg                                            20

<210> SEQ ID NO 29
<211> LENGTH: 19
<212> TYPE: DNA
```

<400> SEQUENCE: 21
acgtctgttt cagtgct                                               17

```
<400> SEQUENCE: 29
acctggttga tcctgccag                                              19

<210> SEQ ID NO 30
<211> LENGTH: 21
<212> TYPE: DNA
<213> ORGANISM: synthetic construct

<400> SEQUENCE: 30
cttccgcagg ttcacctacg g                                           21

<210> SEQ ID NO 31
<211> LENGTH: 20
<212> TYPE: DNA
<213> ORGANISM: synthetic construct

<400> SEQUENCE: 31
aagttgcgta aatagagccc                                             20

<210> SEQ ID NO 32
<211> LENGTH: 20
<212> TYPE: DNA
<213> ORGANISM: synthetic construct

<400> SEQUENCE: 32
caagacatcc attgctgaaa                                             20

<210> SEQ ID NO 33
<211> LENGTH: 18
<212> TYPE: DNA
<213> ORGANISM: synthetic construct

<400> SEQUENCE: 33
acgtctgttt cagtgtct                                               18

<210> SEQ ID NO 34
<211> LENGTH: 20
<212> TYPE: DNA
<213> ORGANISM: synthetic construct

<400> SEQUENCE: 34
aaattcagcg ggtaacctcg                                             20
```

PCR-BASED IDENTIFICATION OF EIMERIA SPECIES AND STRAINS

FIELD OF THE INVENTION

The present invention relates to a PCR-based method of identifying various species of the genus Eimeria (commonly known as coccidia). More particularly, the present invention relates to a PCR-based method which is genus-specific, utilises novel PCR primers, and has the potential to identify species of Eimeria which may differ only by relatively minor sequence variations.

BACKGROUND OF THE INVENTION

Bibliographic details of the publications referred to herein are collected at the end of the description.

Commonly used abbreviations in this text are: ITS, internal transcribed spacer; ITS-1, first internal transcribed spacer; ITS-2, second internal transcribed spacer; rDNA, ribosomal DNA; TBE, Tris-borate-EDTA; DPGE, denaturing polyacrylamide gel elctrophoresis; SSCP, single-strand conformation polymorphism.

Coccidiosis is a disease of animals and birds caused by protozoan parasites known as coccidia (Eimeria). This disease is of major economic importance for the poultry industry world-wide.

Eimeria species have complicated life cycles, details of which are well described. Briefly, when a sporulated (infective) coccidial oocyst is ingested, sporozoites are released to initiate asexual and sexual cycles that lead to the production of thousands of new oocysts, which are shed in the faeces of the host. These oocycts sporulate in the environment within days and then are infectious to naive birds. A single sporulated oocyst may give rise to thousands of progeny. Eimeria species produce lesions in the gut by destruction of the epithelial cells in which they develop and multiply, and cause trauma to the intestinal wall.

The clinical signs of coccidiosis include diarrhoea, which may be mucoid or bloody, and dehydration. These symptoms are generally followed by ruffled feathers, anaemia, listlessness, loss of weight, retraction of the head and neck and somnolence. Coccidiosis in laying hens is usually detected by a decrease in egg production. Infected growing birds, soon cease to grow satisfactorily. With highly virulent strains of Eimeria morality in chickens is generally very high.

Currently, seven species of Eimeria are recognised to infect chickens. These species differ considerably in their biology and pathogenicity (Mc Dougald et al, 1998). Being able to accurately identify Eimeria species and "strains" has major implications for diagnosis and control as well as for studying their epidemiology and population biology.

Traditionally, species of Eimeria have been identified by a variety of methods. For example, morphological features and/or morphometry of their oocysts or sporocysts (size, shape, length and width), their patterns of development, the nature of the lesions they produce, their predilection site(s) in the gut, sporulation times and reproductive index, or from the specific host from which they originate. However, these criteria can be unreliable (Eckert et al, 1995; Andrews and Chilton, 1999). Biochemical, immunological and molecular methods can overcome such limitations (Andrews and Chilton, 1999; Gasser, 1997) but may themselves have other limitations.

Polymerase chain reaction (PCR) methods of identifying species of Eimeria, using appropriate genetic markers, may be used as alternatives to the above mentioned traditional means, because of their ability to specifically amplify minute amounts of parasitic material (Stucki et al, 1993). However, such methods described to date are species-specific and may require the running of a number of different PCR reactions (using distinct pairs of species-specific oligonucleotide primers) in order to correctly identify a particular species of Eimeria.

For the molecular identification and classification of organisms analysis of critical specific genomic regions is required. One such region in eukaryotes is a part of the nuclear genome within the ribosomal DNA (rDNA) gene family. The rDNA of eukaryotes is a multigene family consisting of tandemly repeated units. Each unit comprises, an external transcribed spacer (ETS), the genes encoding the 18S, 5.8S and 28S rRNAs, separated by internal transcribed spacer regions (ITS-1 and ITS-2, respectively), and an intergenic spacer (IGS). Within this region the sequences of ITS-1 and ITS-2 provide reliable genetic markers for the identification of organisms to the species level because intraspecific variation in these sequences is usually low compared with higher levels of interspecific difference.

It has been demonstrated that ITS-1 and ITS-2 are useful genetic markers for the identification of species of Eimeria (Tsuji et al, 1997; Molloy et al, 1998; Schnitzler et al, 1999) or detection of population variation (Barta et al, 1998).

A PCR-based assay using species-specific primers in the ITS-1 for the typing of samples to species based on the detection of a product of a particular size on agarose gels has been developed (Schnitzler et al, 1999). However, such an assay does not allow sequence variation within a specific PCR product to be analysed and may further be disadvantaged by the fact that it is species-specific.

Further, Barta et al, 1998 have used a cloning/sequencing approach for the analysis of sequence variation both in the ITS-1 and ITS-2 sequences within E. maxima. Again, however, this approach may have limitations, especially where a large number of samples are to be analysed, as it is labour-intensive, time consuming and costly to perform. Moreover, it does not necessarily accurately define sequence variation among the different copies of rDNA, is species-specific, and can introduce artefacts into sequence data (Gasser, 1997).

Due to the economic impact of coccidiosis on the poultry industry, for example, it is important that species of Eimeria are readily identifiable, such that rapid diagnosis of disease and treatment may occur. Further, sensitive and reliable identification of Eimeria is desirable for the study of the epidemiology of the diseases and for controlling the purity of laboratory lines of Eimeria. Accordingly, there is a need to develop an assay for the rapid identification of species of Eimeria which does not have the limitations of previously described assays.

BRIEF SUMMARY OF THE INVENTION

In one broad aspect of the present invention there is provided an oligonucleotide primer comprising at least 15 consecutive bases of the DNA sequence designated WW1 (SEQ ID NO: 31).

Preferably, the oligonucleotide primer comprises the sequence designated WW1 (SEQ ID NO: 31).

In a second broad aspect of the present invention there is provided an oligonucleotide primer comprising at least 15 consecutive bases of the DNA sequence designated WW3r (SEQ ID NO: 32).

Preferably, the oligonucleotide primer comprises the sequence designated WW3r (SEQ ID NO: 32).

In a third broad aspect of the present invention there is provided an oligonucleotide primer comprising at least 15 consecutive bases of the DNA sequence designated WW2 (SEQ ID NO: 33).

Preferably, the oligonucleotide primer comprises the sequence designated WW2 (SEQ ID NO: 33).

In a forth broad aspect of the present invention there is provided an oligonucleotide primer comprising at least 15 consecutive bases of the DNA sequence designated WW4r (SEQ ID NO: 34).

Preferably, the oligonucleotide primer comprises the sequence designated WW4r (SEQ ID NO: 34).

In a further broad aspect of the present invention there is provided a pair of PCR primers, one primer comprising at least 15 consecutive bases of the DNA sequence designated the WW1 (SEQ ID NO: 31) and a second primer comprising at least 15 consecutive bases of the DNA sequence designated WW3r (SEQ ID NO: 32).

Preferably, said pair of PCR primers comprises one primer comprising the DNA sequence designated WW1 (SEQ ID NO: 31) and a second primer comprising the DNA sequence designated WW3r (SEQ ID NO: 32).

In a further broad aspect of the present invention there is provided a pair of PCR primers, one primer comprising at least 15 consecutive bases of the DNA sequence designated WW2 (SEQ ID NO: 33) and a second primer comprising at least 15 consecutive bases of the DNA sequence designated WW4r (SEQ ID NO: 34).

Preferably, said pair of PCR primers comprises a primer comprising the DNA sequence designated WW2 (SEQ ID NO: 33) and a primer comprising the DNA sequence designated WW4r (SEQ ID NO: 34).

Preferably, said pairs of PCR primers as described herein are adapted to amplify specified regions of the rDNA of Eimeria in a genus-specific manner.

In a third broad aspect of the present invention there is provided a method of identifying Eimeria in a sample, said method comprising the steps:

providing a sample comprising genomic template DNA to be tested;

providing genomic DNA of one or more standards of known identity;

providing a pair of PCR primers selected from the group consisting of
  (i) primers comprising at least 15 consecutive bases of the DNA sequence designated the WW1 (SEQ ID NO: 31) and WW3r (SEQ ID NO: 32); or
  (ii) primers comprising at least 15 consecutive bases of the DNA sequences designated WW2 (SEQ ID NO: 33) and WW4r (SEQ ID NO: 34); and amplifying by means of PCR a region of template DNA using said primer pair to produce one or more PCR products from said sample, and said one or more standard of known identity;

comparing said one or more PCR products derived from said sample against one or more PCR products of said one or more standard of known identity; and identifying the species of Eimeria present within the sample.

Preferably, said pair of PCR primers comprises the primers comprising the sequences designated WW1 (SEQ ID NO: 31) and WW3r (SEQ ID NO: 32).

Alternatively, said pair of PCR primers comprises the primers comprising the sequences designated WW2 (SEQ ID NO: 33) and WW4r (SEQ ID NO: 34).

Preferably, two PCRs are run per sample to be tested, wherein each PCR uses a different primer pair.

Alternatively, one PCR is run per sample to be tested and both primer pairs are provided within said one PCR.

Preferably said one or more PCR products derived from said sample are compared against said one or more PCR products of said one or more standard of known identity by means of gel electrophoresis.

Preferably, the gel electrophoresis is DPGE.

More preferably, the gel electrophoresis is SSCP.

Alternatively, both DPGE and SSCP may be employed.

In a further aspect of the present invention there is provided the use of any one of the PCR primers as herein described for the identification of species of Eimeria.

The invention may also be said broadly to consist in the parts, elements and features referred to or indicated in the specification of the application, individually or collectively, in any or all combinations of 2 or more of said parts, elements or features, and where specific integers are mentioned herein which have known equivalents in the art to which the invention relates, such known equivalents are deemed to be incorporated herein as if individually set forth.

FIGURES

These and other aspects of the present invention, which should be considered in all its novel aspects, will become apparent from the following description, which is given by way of example only, with reference to the accompanying figures, in which:

FIG. 1 Illustrates E. tenella ITS-1 sequence amplified with primer pair WW1 and WW3r (shown in italics), the underlined sequence represents ITS-1 and plain text sequence the 3' end of 18s rDNA and 5' end of 5.8s rDNA (SEQ ID NO: 1);

FIG. 2 Illustrates E. tenella ITS-2 sequence amplified with primer pair WW2 and WW4r (shown in italics), the underlined sequence represents ITS-2 and plain text sequence the 3' end of 5.8s rDNA and 5' end of 28s rDNA (SEQ ID NO: 2);

Figure 3:
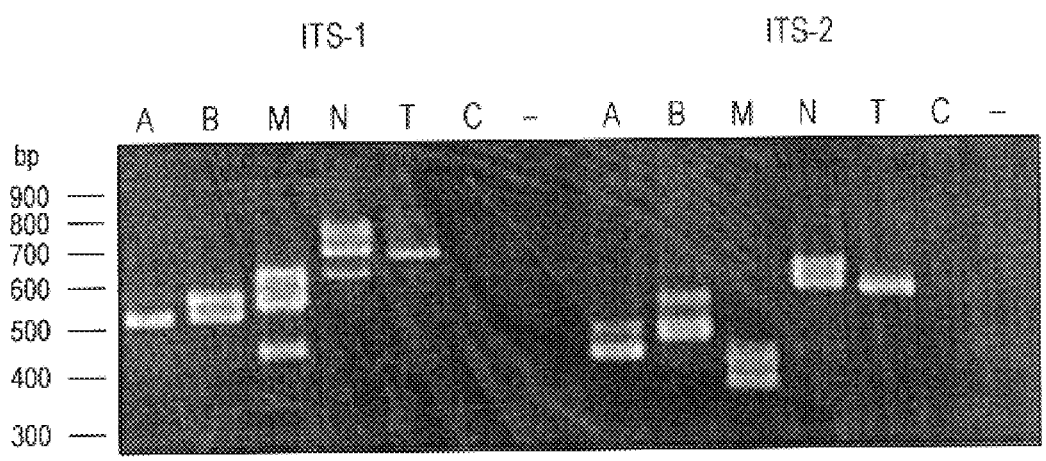
Figure 4A:
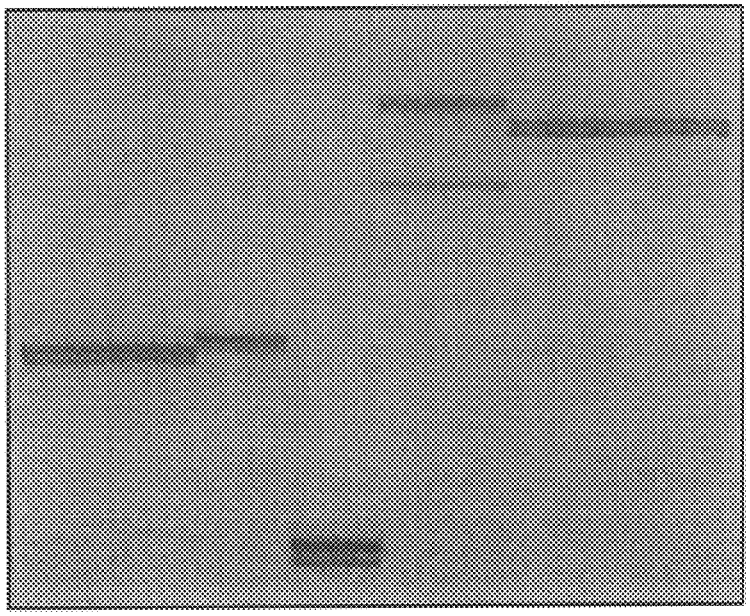
Figure 4B:
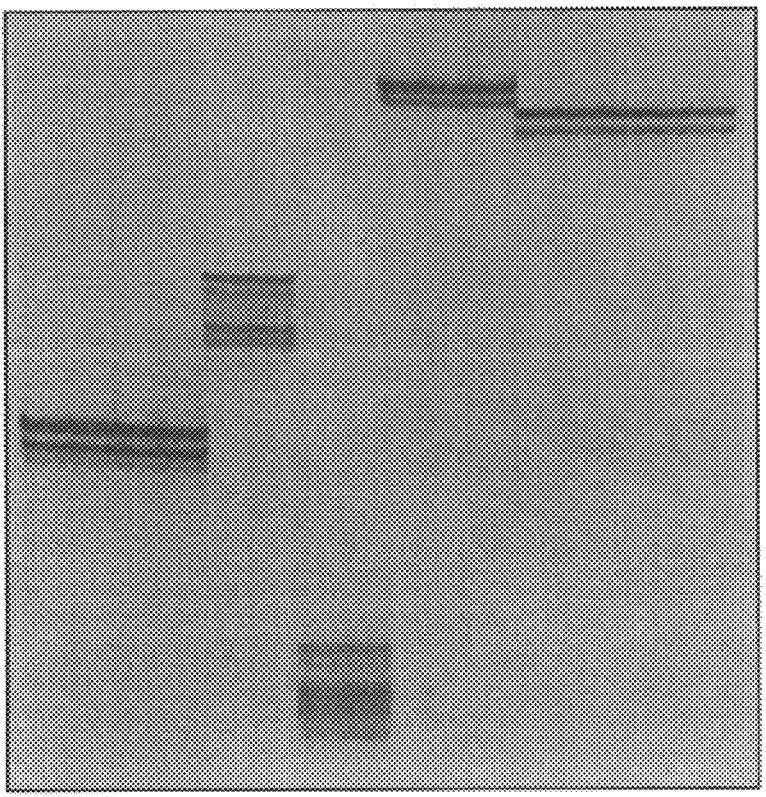
Figure 5A:
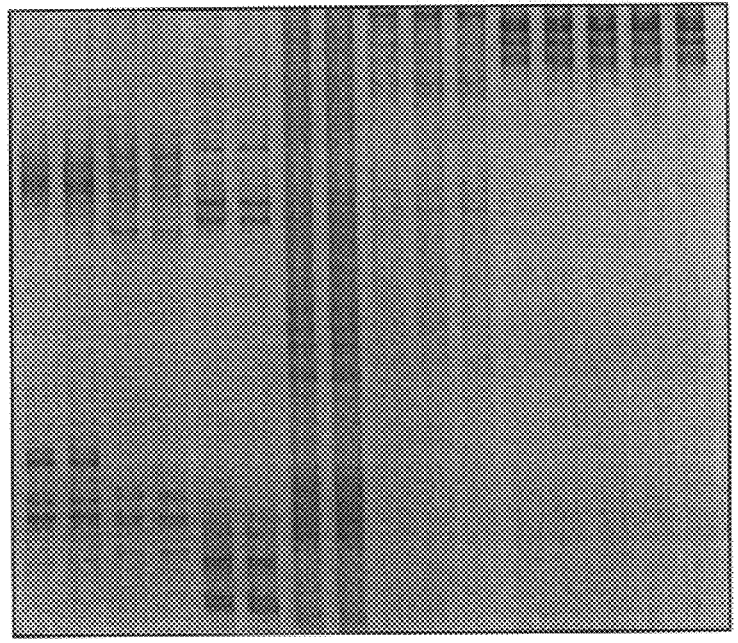
Figure 5B:
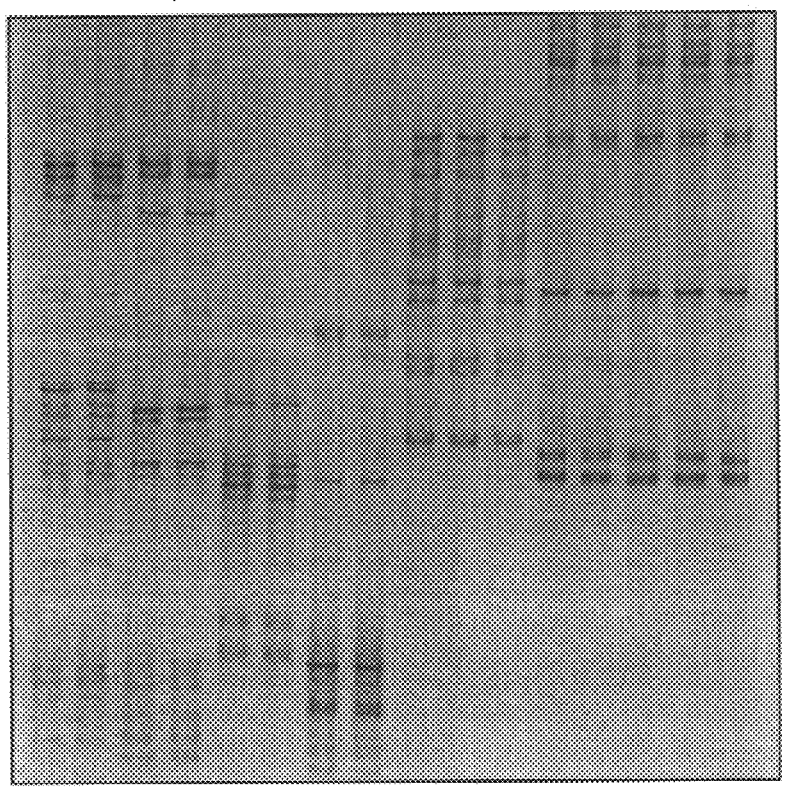
Figure 6A:
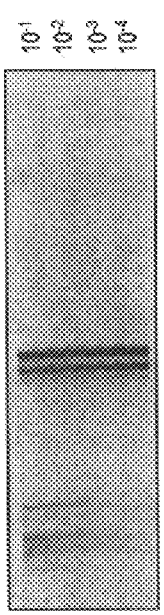
Figure 6B:
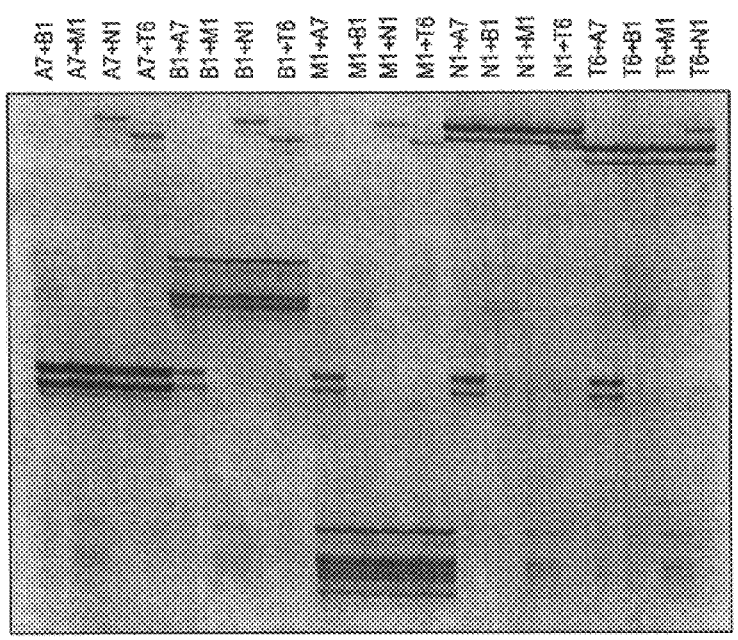

FIG. 3 Agarose gel showing ITS-1 or ITS-2 PCR products representing E. acervulina, E. brunetti, E. maxima, E. necatrix, E. tenella (A, B, M, N and T, respectively). Chicken DNA and no DNA controls (C and -, respectively);

FIGS. 4A–4B DPGE analysis of ITS-1(FIG. 4A) or ITS-2(FIG. 4B) PCR products amplified from multiple oocyst isolates representing five species of Eimeria from chickens, in the following order: E. acervulina (isolates A7, A2, A12 and A3), E. brunetti (isolates B1 and B5), E. maxima (isolates M1 and M2), E. necatrix (isolates N1, N5 and N10) and E. tenella (isolates T6, T5, T7, T3 and T4) (cf. Table 1);

FIGS. 5A–5B SSCP analysis of ITS-1(FIG. 5A) or ITS-2(FIG. 5B) PCR products amplified from multiple oocyst isolates representing five species of Eimeria from chickens, in the following order: E. acervulina (isolates A7, A2, A12 and A3), E. brunetti (isolates B1 and B5), E. maxima (isolates M1 and M2), E. necatrix (isolates N1, N5 and N10) and E. tenella (isolates T6, T5, T7, T3 and T4) (see Table 1);

FIGS. 6A–6B Ability of the DPGE approach to specifically detect multiple species of Eimeria within samples. FIG. 6A shows the detection of Eimeria maxima in the presence of excess E. acervulina (DNA of isolates A7 to M1 mixed in ratios of $1:10^{-1}$, $1:10^{-2}$, $1:10^{-3}$ and $1:10^{-4}$). FIG. 6B shows the detection of a particular species (second isolate) in the presence (+) of 100×excess DNA of a heterologous species (first isolate), for all possible species combinations presented. *E. acervulina, E. brunetti, E. maxima, E. necatrix* and *E. tenella* represented by isolates A7, B1, M1, N1 and T6, respectively (see Table 1).

DETAILED DESCRIPTION OF THE INVENTION

The following is a description of the preferred forms of the present invention given in general terms in relation to the application of the novel PCR primers herein described to a method of identifying species of Eimeria. The invention is further elucidated from the disclosure given under the sub-heading "Experimental Basis of the Invention" below, which provides examples of preferred forms of the invention.

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein "genus" is used to refer to a principal rank in the taxonomic hierarchy, falling below the family level and above the species level; "species" is used to refer to a fundamental rank in the taxonomic hierarchy falling below the genus level and indicating the limit of organisms able to interbreed; and "strain" is used to refer to a taxonomic level below the species level, which may indicate population variation within a species. Accordingly, PCRs referred to as "species-specific" are those which are adapted to amplify designated regions of DNA from a single species only. Those PCRs referred to as "genus-specific" are adapted to amplify designated regions of DNA from a number of species within a particular genus.

In a preferred form of the present invention, faecal samples obtained from chickens are processed such that the genomic DNA of any parasitic element present in the sample is isolated. It will be appreciated that any method suitable for the isolation of genomic DNA of Eimeria may be used, however, a preferred method is described under the heading "Experimental Basis of the Invention; 1 Parasites and Isolation of Genomic DNA".

DNA isolated as above mentioned is subsequently used as a template in a PCR using either of the novel PCR primer pairs of the invention; WW1 (SEQ ID NO: 31) and WW3r (SEQ ID NO: 32), or, WW2 (SEQ ID NO: 33) and WW4r (SEQ ID NO: 34). The sequences of each of these primers is provided under the sub-heading "Experimental Basis of the Invention; 2 Enzymatic amplification of rDNA" and the position of each of the primers in relation to ITS1 and ITS2 of Eimeria rDNA is depicted in FIGS. 1 and 2, respectively. The primer pairs of the present invention enable genus-specific PCR amplification of Eimeria ITS DNA and thus each pair is applicable to any sample of suspected coccidia and the identification of any number of different species within the genus Eimeria.

According to the invention, a PCR primer (or, an oligonucleotide primer) is an oligonucleotide capable of specific hybridisation under particular PCR conditions to a region of the template DNA, which has a sequence which is substantially complementary to the primer sequence, and is adapted to prime the extension of DNA during PCR. It will be realised that a complementary sequence is capable of forming Watson-Crick bonds with its complement, in which adenine pairs with thymine or guanine pairs with cytosine. Each primer is typically used as a member of a primer pair, including a 5' upstream primer that hybridises with the 5' end of the template DNA to be amplified and a 3' downstream primer that hybridises with the complement of the 3' end of the template DNA to be amplified.

Those of ordinary skill in the art to which the invention relates will understand that the term "substantially complementary", as used herein, means that the primer may not have 100% complementarity to its target template sequence but is still capable of annealing thereto in a specific manner under appropriate PCR annealing conditions.

The primers of the present invention may be prepared by any number of conventional DNA synthesis methods. In the present case, the primers were manufactured and purchased commercially from Genset Pacific Pty Limited, PO Box 3088, Lismore, NSW 2480, Australia.

In accordance with the preferred embodiment, optimal results have been obtained using primers which are identical in length and sequence to the primers WW1 and WW3r and/or, WW2 and WW4r as abovementioned. However, a person of ordinary skill in the art will recognise that alterations may be made to the primers while still maintaining the genus-specificity of the PCR amplification and the efficacy of the present inventive diagnostic method.

Firstly, the length of the primers used may be varied. For example, the present invention contemplates that shorter primers containing at least 15 consecutive bases of the nucleotide sequences of these primers may be suitable. Similarly, the primers may be lengthened. The exact upper limit of the length of the primers is not critical. However, typically primers will be less than or equal to approximately 30 bases and preferably less than or equal to 26 bases. By way of example, it is considered that primer WW1 may be extended by up to 10 nucleotides from its 3' end (TCT AAA GGA T (SEQ ID NO: 3)), WW2 may be extended by up to 4 nucleotides at its 5' end (CAGC (SEQ ID NO: 4)), WW3r may be extended by up to 5 nucleotides from its 3' end (GTT TT (SEQ ID NO: 5)) or up to 10 nucleotides from its 5' end (ATG CGT GAG C (SEQ ID NO: 6)) and WW4r may be extended by up to 10 nucleotides at either end (3' end, ACT GAT TTC A (SEQ ID NO: 7) and 5' end, TGA TAT GCT T (SEQ ID NO: 8)). In addition, non-complementary nucleotide fragments may also be attached to the 5' end of the primers, effectively increasing their length.

Secondly, the present invention contemplates minor changes (or conservative alterations) to the sequence of the primers which do not substantially alter their ability to anneal to their specific target DNA and subsequently prime extension during PCR. For example, any particular nucleotide, or plurality of nucleotides, of a primer may be substituted for alternative nucleotides, which may not allow for Watson-Crick base-pairing at the particular site of alteration on annealing of the primer to the template DNA during PCR, but nonetheless does not substantially affect the ability of the primer to prime extension during PCR. Such alternative primers may be referred to as "annealing equivalents" of the primers WW1, WW3r, WW2 or WW4r and variants thereof, as described herein. Such annealing equivalents will be at least 15 nucleotides in length and adapted to anneal to a target sequence under appropriate PCR annealing conditions. Generally, appropriate PCR annealing conditions for such annealing equivalents include the use of a PCR reaction mix or buffer having 3–7 mM $MgCl_2$. It is considered that annealing temperatures of between 45° C. and 52° C. may be appropriate for most annealing equivalents. By way of further exemplification, if 5 nucleotides within a particular primer sequence were altered in a manner described in this paragraph, and those alterations were spread centrally across the primer sequence, the preferred annealing temperature of that primer is likely to drop by approximately 5° C. A target sequence, as referred to in this paragraph, means a sequence being complementary to the sequence of either one of the primers WW1 (SEQ ID NO: 31), WW3r (SEQ ID NO: 32), WW2 (SEQ ID NO: 33) or WW4r (SEQ ID NO: 34).

It will be appreciated that the usefulness of any alternative PCR primer sets designed around WW1 and WW3r, and/or, WW2 and WW4r, of the present invention, may be evaluated, at least notionally, using appropriate software and the ITS-1 and ITS-2 and flanking region DNA sequence information. Such software packages include, for example, PC Oligo5 (National Bioscience Inc) or Amplify (University of Wisconsin).

Examples of variations on the primers WW1 (SEQ ID NO: 31), WW3r (SEQ ID NO: 32), WW2 (SEQ ID NO: 33) and WW4r (SEQ ID NO: 34) which may be appropriate in the present invention include:

| Variations of WW1 (5'-3') | Variations of WW3r (5'-3') |
|---|---|
| AGTTGCGTAAATAGAGCCC (SEQ ID NO:9) | AAGACATCCCATTGCTGAAA (SEQ ID NO:10) |
| AAGTTGCGTAAAAG AGCC (SEQ ID NO;11) | CAAGACATCCATTGC TGAA (SEQ ID NO:12) |
| AAGTTGCGTAAATAGAGC (SEQ ID NO:13) | CAAGACATCCATTGCTGA (SEQ ID NO:14) |
| TTGCGTAAATAGAGCCC (SEQ ID NO:15) | GACATCCATTGCTGAAA (SEQ ID NO:16) |

| Variations of WW2 (5'-3') | Variations of WW4r (5'-3') |
|---|---|
| CGTCTGTTTCAGTGTCT (SEQ ID NO:17) | AATTCAGCGGGTAACCTCG (SEQ ID NO:18) |
| ACGTCTGTTTCAGTGTC (SEQ ID NO:19) | AAATTCAGCGGGTAACCTC (SEQ ID NO:20) |
| ACGTCTGTTTCAGTG CT (SEQ ID NO:21) | AAATTCAGCGGGTAACCT (SEQ ID NO:22) |
| GTCTGTTTCAGTGTCT (SEQ ID NO:23) | TTCAGCGGGTAACCTCG (SEQ ID NO:24) |

While the novel primers disclosed herein have been designed to enable genus-specific PCR amplification of regions of ITS-1 and ITS-2, it will be appreciated that they may also be applied, individually or in combination, to various other applications. For example they may be used as molecular probes, or primers for alternative diagnostic techniques (such as LCR, ligase chain reaction).

Generally, only one PCR, using a single primer set, will be needed in order to identify the species of Eimeria present within a sample. However, it will be appreciated that there may be times where a parallel PCR, using the second primer set, may be utilised in order to further clarify the identity of a species present within a sample. Similarly, upon optimisation of the PCR conditions both novel primer sets may be used in a single PCR.

In order that the PCR products may subsequently be detected, the primers are preferably end-labelled with [γ-$^{33}$P]ATP. Alternatively, other means of labelling the PCR products may be utilised; for example, incorporation of [α-$^{32}$P]dNTPs during PCR amplification, or, non-radioactive labelling systems using digoxygenin, biotin and the like, may be employed.

Each PCR is run with at least one monospecific control sample or standard of known species identity. It will be appreciated that control samples containing more than one known species may be entertained. Negative controls in which no Eimeria template DNA is present are also run against the samples. It will be appreciated that other standard controls routinely used in the art may also be run against the samples.

The Eimeria genomic DNA of the control or standards of known Eimeria species may be purified in a like manner to the genomic DNA of unknown samples. Laboratory lines of known Eimeria identity obtained from Medichick Laboratories (Australia) or Animal Research Institute of the Queensland Department of Primary Industries (Australia), for example, may be utilised for this purpose.

Amplification is conducted according to conventional procedures in the art to which this invention relates; such as described in U.S. Pat. No. 4,683,202. Preferably standard PCRs according to the invention include 0.1 $\mu$M–1 $\mu$M of each primer, 200 $\mu$M each dNTP, 3–7 mM MgCl$_2$, and 1 U Taq DNA polymerase (Promega). Typically, each PCR is overlayed with mineral oil or the like to prevent evaporation of the reaction mix during cycling. PCR cycling is preferably run under the following conditions: denaturation at a temperature of 94° C. for 30 seconds, annealing at a temperature of from 45° C. to 60° C. for 30 seconds and extension at a temperature of 72° C. for 30 seconds. Preferably between 30 and 35 cycles are run. More specifically, the following PCR conditions may be for the preferred pairs of primers, WW1 and WW3r, and WW2 and WW4r, of the invention:

| Denaturation | Annealing | Extension | Cycles |
|---|---|---|---|
| 94° C., 30 seconds | 45° C., 30 seconds | 72° C., 30 seconds | 30 |
| 94° C., 30 seconds | 50° C., 30 seconds | 72° C., 30 seconds | 30 |
| 94° C., 30 seconds | 60° C., 30 seconds | 72° C., 30 seconds | 30 |

It will be appreciated by those of ordinary skill in the art that the PCR conditions provided herein are merely exemplary and may be varied so as to optimise conditions where, for example, alternative PCR cyclers or DNA polymerases are used, where the quality of the template DNA differs, or where variations of the primers not specifically exemplified herein are used, without departing from the scope of the present invention. The PCR conditions may be altered or optimised by changing the concentration of the various constituents within the reaction and/or changing the constituents of the reaction, altering the number of amplification cycles, the denaturation, annealing or extension times or temperatures, or the quantity of template DNA, for example. Those of skill in the art will appreciate there are a number of other ways in which PCR conditions may be optimised to overcome variability between reactions.

It will be understood that where no specifically exemplified herein appropriate PCR annealing temperatures for any primer within the scope of the present invention may be derived from the calculated melting temperature of that primer. Such melting temperatures may be calculated using standard formulas, such as that described in Sambrook, 1989. As will be understood by those of ordinary skill in the art to which this invention relates annealing temperatures may be above or below the melting temperature but generally an annealing temperature of approximately 5° C. above the calculated melting temperature of the primer may be suitable.

PCR products, obtained from the amplification of regions of ITS-1 and ITS-2 of both unknown samples and relevant control samples or standards of known identity, may be detected by electrophoretic separation. Electrophoretic techniques which are particularly sensitive to minor differences in PCR product size and/or sequence are preferred. For example, the techniques of SSCP (single-strand conformation polymorphism) and/or DPGE (denaturing polyacrylamide gel electrophoresis) are particularly suitable when conditions are optimised as they have the ability to detect single base changes in sequence or variation in length by a single nucleotide between samples. In addition, these techniques are readily applicable to the screening of large numbers of samples.

SSCP analysis has been described (Orita et al, 1989). Generally, any particular PCR product may be separated as single-stranded molecules by electrophoresis in a non-denaturing polyacrylamide gel. The technique is based on the fact that a molecule of single-stranded DNA folds differently from another such molecule if it differs in sequence by a single base or more; differences in tertiary structure result in differences in mobility during electrophoresis.

Those of ordinary skill in the art to which this invention relates will understand that the tertiary structure of single-stranded DNA changes under different physical conditions, for example, temperature and ionic environment. As a result, the sensitivity of SSCP depends on these and many other such conditions, such as the length of the PCR product. In the case of the present invention, the following conditions have been found to be preferred, however, it will be appreciated that the conditions may be altered to take account of different laboratory conditions and equipment; 0.4 to 0.6× MDE (mutation detection enhancement; FMC BioProducts) containing 0.5 to 1.5×TBE and electrophoresis performed at 7 to 40 W for approximately 17 hours at 15° C. More specifically, the following conditions may be utilised in the invention:

| Gel | Power (W) | Time (hours) | Temperature (° C.) |
|---|---|---|---|
| 0.5x MDE containing 0.6x TBE | 7 | 17 | 15 |
| 0.4x MDE containing 0.6x TBE | 7 | 17 | 15 |
| 0.6x MDE containing 0.6x TBE | 20 | 17 | 15 |
| 0.6x MDE containing 0.6x TBE | 30 | 17 | 15 |
| 0.6x MDE containing 0.6x TBE | 40 | 17 | 15 |
| 0.6x MDE containing 0.5x TBE | 20 | 17 | 15 |
| 0.6x MDE containing 1.0x TBE | 30 | 17 | 15 |
| 0.6x MDE containing 1.5x TBE | 40 | 17 | 15 |

DPGE has previously been described and is well known in the art to which this invention relates. In DPGE each strand of a DNA molecule is separated from its complementary strand and run on a polyacrylamide gel under denaturing conditions. Under such conditions, the two strands of any particular DNA molecule are prevented from re-hybridising to one another during electrophoresis such that individual strands will migrate separately within the gel. DPGE is a sensitive system which is capable of identifying differences in the length of any two DNA molecules to a single nucleotide.

In the case of DPGE, the following range of conditions are preferable, however, as with the SSCP conditions, they may be altered to take account of many other laboratory variables, without departing from the scope of the present invention; 0.4 mm thick gel between 4 and 6% polyacrylamide, containing 42% urea and 1×TBE, subjected to electrophoresis at between 20 to 50 W for approximately 4 hours at 40° C. More specifically, the following conditions may be utilised in the present invention:

| Gel (polyacrylamide) | Power (W) | Time (Hours) | Temperature (° C.) |
|---|---|---|---|
| 0.4 mm thick (6%) containing 42% urea and 1x TBE | 40 | 4 | 40 |
| 0.4 mm thick (4%) containing 42% urea and 1x TBE | 40 | 4 | 40 |
| 0.4 mm thick (5.5%) containing 42% urea and 1x TBE | 40 | 4 | 40 |
| 0.4 mm thick (5%) containing 42% urea and 1x TBE | 20 | 4 | 40 |
| 0.4 mm thick (5%) containing 42% urea and 1x TBE | 30 | 4 | 40 |
| 0.4 mm thick (5%) containing 42% urea are 1x TBE | 50 | 4 | 40 |

It should be noted that DPGE is preferred for species identification while SSCP is preferred for the detection of population variation within a species, although both techniques are applicable to species identification. Thus, it will be appreciated that either one of SSCP or DPGE may be used alone to effect identification or diagnosis of Eimeria species. However, the present invention also contemplates both techniques being used in parallel in order to gain a better understanding of the identity of the species of Eimeria within a particular sample. Similarly, the present invention considers the use of other complementary techniques such as agarose gel electrophoresis and DNA sequencing.

Following separation of PCR products via electrophoresis, gels may be processed according to standard techniques (for example, in the case of polyacrylamide gels, dried on to filter or blotting paper), and subjected to autoradiography for a time appropriate to be able to demonstrate the position of the PCR product bands on a gel.

The methodology of the present invention may be adapted to an automated (fluorescence-based) electrophoretic system; for example, and Applied BioSystems (ABI) automated sequencing apparatus coupled with appropriate computer hard- and software. In this way, specific "fingerprints" for individual species of Eimeria may be recorded, stored (for protocol and reporting purposes) and compared against standard samples of known species status.

EXPERIMENTAL BASIS OF THE INVENTION

1. Parasites and isolation of genomic DNA

Australian isolates of Eimeria (representing monospecific lines; Table 1) were passaged in specific pathogen free (SPF) chickens maintained in custom-built isolators under stringent conditions to prevent cross-contamination. Isolates were identified to species based on the morphometry of sporulated oocysts, prepatent period and location of gross lesions in the intestine(s). To rule out putative contamination of isolates with one or more heterologous species, the 18S rRNA gene, which also provides species-level identification (Barta et al, 1997), was sequenced from PCR products derived from selected oocyst isolates (see 4 below). The 18S sequences determined for individual species had 99–100% identity with those published recently by other workers (Barta et al, 1997).

For each isolate, feces were collected from groups of chickens and the Eimeria oocysts allowed to sporulate under constant aeration at 30° C. for a minimum of 48 hours. Oocysts were isolated using saturated NaCl (Shirley et al, 1995), washed extensively in 50 ml volumes of $H_2O$ and made up to a final aqueous suspension (10 ml containing $5\times10^6$ oocysts). The oocysts were then purified using a sucrose-gradient centrifugation method (Gasser et al, 1987), which removed fecal components inhibitory to the PCR, washed (as above) and then resuspended in 1 ml of $H_2O$. DNA was isolated from oocytes using a Wizard® Genomic DNA Purification Kit (Promega, Wis., USA). In brief, each aqueous suspension of oocysts was transferred to a 1.5 ml Eppendorf tube, centrifuged at 13000 g for 5 min and resuspended in 300 µl of Nuclei Lysis Solution (Promega, Wis., USA). An equal volume of glass beads (2 mm in diameter) was added and the tube vortexed vigorously for 3–5 min until >90% of the oocysts ruptured (assessed by light microscopic examination of a tiny sub-aliquot at 400× magnification). The suspension containing sporocysts was then transferred to a fresh Eppendorf tube, the glass beads discarded, proteinase K (150 µg ml$^{-1}$) and sodium dodecyl-sulfate (5% w/v) added, and then incubated at 37° C. until >90% of the sporocysts had ruptured (~4 h). This lysate was then centrifuged at 13000 g for 5 min to pellet the oocyst and sporocyst walls, and the supernatant transferred to a fresh tube. The DNA was purified from the supernatant according to the "yeast DNA protocol" (Promega) and eluted into 50 µl of $H_2O$. Individual samples were checked on ethidium bromide-stained 2% agarose-Tris-Borate-EDTA (TBE=65 mM Tris-HCl, 27 mM boric acid, 1 mM EDTA, pH 9; Bio-Rad, Richmond, Calif., USA) gels using specific dilutions of phage λ DNA (Promega, Wis., USA) as markers, which were also used to approximate DNA concentrations. The amounts of genomic DNA isolated from individual isolates (~$5\times10^6$ oocysts) were estimated at 1–2.5 µg.

specific for the genus Eimeria. The ITS-1 (plus flanking sequence) was amplified by PCR using the primers WW1 (forward: 5'-AAG TTG CGT AAA TAG AGC CC-3' (SEQ ID NO: 25)) and WW3r (reverse: 5'-CAA GAC ATC CAT TGC TGA AA-3' (SEQ ID NO: 26)), while ITS-2 was amplified using the primers WW2 (forward: 5'-ACG TCT GTT TCA GTG TCT-3' (SEQ ID NO: 27)) and WW4r (reverse: 5'-AAA TTC AGC GGG TAA CCT CG-3' (SEQ ID NO: 28)). The 18S gene was amplified using primers WW5 (5'-ACC TGG TTG ATC CTG CCA G-3' (SEQ ID NO: 29)), and WW6r (5'-CTT CCG CAG GTT CAC CTA CGG-3' (SEQ ID NO: 30)). Primers used to amplify ITS-1 or ITS-2 were endlabelled with [γ-$^{33}$P]ATP (NEN Life Science Products) using T4 polynucleotide kinase according to the manufacturer's protocol (Promega, Wis., USA). PCR reactions were performed in 30 µl volumes using ~50 ng of template, 50 pmol primer, 200 µM of each dNTP, 7 mM $MgCl_2$ (for ITS-1) or 3 mM $MgCl_2$ (for ITS-2) and 1 U Taq DNA polymerase (Promega, Wis., USA) under the following thermocycling conditions: 94° C., 30 s (denaturation); 55° C., 30 s (annealing); 72° C., 30 s (extension) for 30 cycles in a DNA Thermal Cycler 480 (Perkin Elmer, USA). Control samples without DNA were included in each PCR run. Also, the specificity of the PCR for both primer sets was tested using DNA (~100 ng) from chicken musculature and faeces (known to be free of Eimeria), and no PCR products were detected in any of those control samples after autoradiography of DPGE gels for 24 h.

Individual PCR products were mixed with an equal volume of loading buffer (10 mM NaOH, 95% formamide, 0.05% bromophenol blue and 0.05% xylene cyanol) and their intensity checked on ethidium bromide-stained 2.5% agarose-TBE gels using 100 bp ladder (Promega, Wis., USA) as a size marker. The lowest amount of Eimeria DNA required for effective amplification (for both primer sets) and visual detection on agarose gels was ~5 pg (represents ~5–50 oocysts), which is comparable with previous studies (Stucki et al, 1993; Schnitzler et al, 1998; Molloy et al, 1998).

TABLE 1

Isolates representing different species of Eimeria. All isolates were derived from chicken flocks in Australia and were maintained as monospecific lines. The MCK lines were provided by Medichick Laboratories (Australia); the others were obtained from the Animal Research Institute of the Queensland Department of Primary Industries (Australia).

| Isolate | Species | Description and geographical origin in Australia |
| --- | --- | --- |
| A7 | E. acervulina | Attenuated RA line derived from a Queensland flock [11] |
| A2 | E. acervulina | 6th passage of A7 |
| A12 | E. acervulina | 15 year old lab line (MCK) derived from a Victorian flock |
| A3 | E. acervulina | 1st passage of A12 |
| B1 | E. brunetti | Attenuated line (AM) derived from a Queensland flock |
| B5 | E. brunetti | 5th passage of B1 |
| M1 | E. maxima | 15 year old lab line (MCK) derived from a Victorian flock |
| M2 | E. maxima | 2nd passage of M1 |
| N1 | E. necatrix | 15 year old lab line (MCK) derived from a Victorian flock |
| N5 | E. necatrix | 2nd passage of N1 |
| N10 | E. necatrix | 8th passage of attenuated derivative of N1 |
| T6 | E. tenella | Field isolate (DARRYL) from Queensland |
| T5 | E. tenella | 4th passage of T6 |
| T7 | E. tenella | Attenuated laboratory line (Rt3 + 15) |
| T3 | E. tenella | 4th passage of T7 |
| T4 | E. tenella | 15 year old lab line (MCK) derived from a Victorian flock |

2. Enzymatic amplification of rDNA

Oligonucleotide primers were designed to regions of the 18S, 5.8S and 28S rRNA gene sequences considered to be 3. High resolution electrophoresis PCR products were denatured at 95° C. for 5 min and snap-cooled on a freeze block (−20° C.) for 2 min before loading on to gels. For DPGE, 5 μl of each sample were loaded into the wells of a 0.4 mm thick, 5% polyacrylamide gel containing 42% urea and 1×TBE, and subjected to electrophoresis at 40 W for 4 h at 40° C. For single-strand conformation polymorphism (SSCP), 3 μl of each sample were loaded into the wells of a 0.4 mm thick non-denaturing gel (0.6×MDE™, mutation detection enhancement; FMC BioProducts, Rockland, Me. USA) containing 0.6×TBE, and electrophoresis performed at 7 W for 17 h at 15° C. Optimization was as described previously (Zhu and Gasser, 1998). Both electrophoretic procedures were performed in a conventional sequencing rig (BaseRunner; IBI, New Haven, Conn., USA). Gels were dried on to blotting paper and subjected to autoradiography using RP1 film (Agfa).

4. DNA sequencing

PCR products were purified over Wizard® PCR Preps columns (Promega, Wis., USA) and eluted into 40 μl H$_2$O. To sequence the 18S rRNA gene, an aliquot (1 μl) was subjected directly to cycle-sequencing with the fmol® DNA Cycle Sequencing System (Promega, Wis., USA) using the same primers as for PCR and an annealing temperature of 55° C. To sequence the ITS-1, an aliquot of column-purified PCR product (100 ng) was cloned into the pGEM®-T plasmid vector (Promega, Wis., USA), and 12 clones (per PCR product) isolated for cycle-sequencing.

5. Results

On agarose gels (FIG. 3), the sizes of ITS-1 PCR products varied from ~450–770 bp, whereas those for the ITS-2 were ~370–620 bp (Table 2). For both ITS-1 and ITS-2, the band size(s) were unique to each species as no intraspecific variation in band profiles was detected between or among multiple isolates. For ITS-1 PCR products, one band was detected for *E. acervulina* and *E. tenella*, whereas 2–3 bands were resolved for the other 3 species (Table 2). For ITS-2 PCR products, one band was detected for *E. tenella*, while 2 bands were displayed for all other species (Table 2). The resolution of multiple ITS bands on agarose gels for some species indicated the existence of different sequence types within a PCR product. This was confirmed by sequencing (via cloning) of the ITS-1 PCR products for selected samples representing each species (A7, B1, M1, N1 and T6, Table 1) and comparison with previously published sequences (Schnitzler et al, 1998; Schnitzler et al, 1999; Barta et al, 1998). Sequencing (of 12 clones per species) showed that individual ITS-1 PCR products represented the appropriate species, although novel ITS-1 sequence types (not shown) were detected for *E. brunetti, E. maxima* and *E. necatrix*.

DPGE and SSCP were then evaluated for their ability to display size and sequence variations in denatured PCR products. Both techniques allowed the unequivocal identification of all five Eimeria species using either ITS-1 and/or ITS-2 PCR products (FIGS. 4A–4B and 5A–5B). For DPGE (FIGS. 4A–4B), the banding profiles were relatively simple, each consisting of 2–5 single-strand bands, with no detectable differences in the number or size(s) of bands between multiple isolates of the same species. As expected based on results of the agarose gel electrophoresis (Table 2), no bands representing a particular species were shared by the heterologous species. Although the ITS-1 banding profiles for *E. acervulina* and *E. brunetti* were similar, the two species could be more readily distinguished using ITS-2. Conversely, *E. necatrix* and *E. tenella* were more easily differentiated using the ITS-1 rather than ITS-2 profile. For SSCP (FIGS. 5A–5B), the banding profiles were relatively complex, each consisting of ~6–15 single-strand bands (depending on ITS region and species). The complex profiles are the result of the formation of multiple conformational types of single-stranded molecule(s). No variation in ITS-1 or ITS-2 profiles was detected among multiple isolates representing the same laboratory line for any of the five species (c.f. Table 1). Similarly, no differences were detected among multiple different laboratory lines for both *E. necatrix* and *E. tenella*. In contrast, a significant difference in ITS-1 and ITS-2 profiles was detected between isolates representing the RA and MCK lines of *E. acervulina*, which remained undetected by DPGE (FIG. 1; lanes A7 and A2 versus lanes A12 and A3). This difference related to polymorphism (or ~1% difference) in both the ITS-1 and ITS-2 sequences between these laboratory lines (unpublished).

TABLE 2

Number and approximate sizes of ITS-1 and ITS-2 PCR PCR products for Eimeria species. Sizes determined in 2.5% agarose in 0.5x TBE by comparison with known size standards. PCR product sizes were interpolated using a formula derived by linear regression of molecular weight standards compared with the log of the imigration distance.

| Species | Number of bands | Approximate sizes of bands (bp) |
|---|---|---|
| ITS-1. | | |
| *E. acervulina* | 1 | 520 |
| *E. brunetti* | 2 | 530, 580 |
| *E. maxima* | 3 | 450, 560, 610 |
| *E. necatrix* | 3 | 630, 715, 770 |
| *E. tenella* | 1 | 700 |
| ITS-2. | | |
| *E. acervulina* | 2 | 440, 490 |
| *E. brunetti* | 2 | 470, 550 |
| *E. maxima* | 2 | 370, 420 |
| *E. necatrix* | 2 | 590, 620 |
| *E. tenella* | 1 | 580 |

6. Specificity of Assay—Multiple Species of Eimeria per Sample

As chickens naturally exposed to Eimeria may simultaneously harbour more than one species of Eimeria (McDougald et al, 1997), it is important to determine the capacity of the procedure to specifically detect DNA in samples containing more than one species. This was tested using ITS-2 as an example. To 20 ng of genomic DNA from each species were added: 2 ng, 200 pg, 20 pg or 2 pg of DNA from a heterologous species (ratios of $1:10^{-1}$, $1:10^{-2}$, $1:10^{-3}$ or $1:10^{-4}$). The DNA template mixes were then subjected to PCR, the PCR products analysed by DPGE and the gels exposed to autoradiographic film (96 h). As an example, the results for *E. acervulina* mixed with differing ratios of *E. maxima* are shown in FIG. 6A. For a template ratio of $1:10^{-4}$, a band representing the first species was detected, while using a template ratio of $1:10^{-3}$ faint bands representing the second species were detectable for most samples (not all results shown). At the dilution ratio of $1:10^{-2}$, the species present at the lower genomic DNA concentration was detected for all combinations (FIG. 6B). These results indicated that the DNA of a particular species was detectable by PCR, even in the presence of excess (100–1000 times the amount) of template from a heterologous species. In addition, DPGE of ITS-2 has been used (in a blind test) to correctly identify all species present in mixed oocyst isolates (FIG. 7), indicating that this technique is useful for detecting mixed-species infections in chickens.

ADVANTAGES AND INDUSTRIAL APPLICABILITY

It will be apparent from the description herein that the assay of the present invention has a number of advantages over previous known techniques used to identify species of Eimeria. For example, the present assay does not require the use of multiple primer sets, specific to each of the species of Eimeria which one wishes to detect, but rather a single genus-specific primer set may be utilised. As a result, multiple species may be co-amplified from a single test sample and run in a single lane on an appropriate electrophoretic gel.

The electrophoretic gel systems (SSCP and/or DFGE) used in the invention to visualise the amplification products, and thus identify the species present within a sample, are extremely sensitive and have the ability to differentiate species which may differ in length by a single nucleotide, or by minor sequence variations.

Further, the techniques offer significant advantages over RAPD-PCR (Johnston et al, 1995; Greif et al, 1996; Shirley et al, 1994 (Paristol Res); Shirley et al, 1994 (Res Vet Sci)) in that they employ well-defined primers to a specific region of rDNA for PCR at relatively high stringency, thereby keeping to a minimum problems with the amplification of contaminating host DNA, and with reproducibility as a consequence of non-specificity of primers and the low annealing temperature in PCR (Ellsworth et al, 1993; MacPherson et al, 1993).

Taken together, the above novel features allow for the rapid, high resolution, qualitative screening of large numbers of samples for any species of the genus Eimeria. Further, the assay obviates the need to conduct DNA sequence analysis (in the first instance), which reduces time, labour and expense.

The assay of the present invention may be used, experimentally or on a commercial scale, as a means of routine diagnosis and monitoring of coccidia, particularly avian coccidia. Alternatively, the assay may be applicable to the quality control of species status of monospecific laboratory lines of Eimeria. It may further be useful as a complementary tool in the development of future commercial vaccines and diagnostic tests.

There is intraspecific and interspecific DNA sequence variation within species of Eimeria. As a result, prior techniques used to detect species of Eimeria have steered clear of utilising anything but species-specific PCRs so as to obviate the need for necessary extensive sequencing and characterisation of resultant PCR products in order to identify isolates, at least at the species level. In contrast the present invention utilises genus-specific PCRs which specifically target variation in sequences both within and between species of Eimeria. This technique has surprisingly proven to be advantageous.

The invention has been described herein, with reference to certain preferred embodiments, in order to enable the reader to practice the invention without undue experimentation. However, a person having ordinary skill in the art will readily recognise that many of the components and parameters may be varied or modified to a certain extent without departing from the scope of the invention. Furthermore, titles, headings, or the like are provided to enhance the reader's comprehension of this document, and should not be read as limiting the scope of the present invention.

BIBLIOGRAPHY

Andrews, R. H. and Chilton, N. B., *Int. J. Parasitol.* 1999, 29, 213–253.

Barta, J. R., Martin, D. S., Liberator, P. A., Dashkevicz, M., Anderson, J. W., Feighner, S. D., Elbrecht, A., Perkins-Barrow, A., Jenkins, M. C., Danforth, H. D., Ruff, M. D. and Profous-Juchelka, H., *J. Parasitol.* 1997, 83, 262–271.

Barta, J. R., Coles, B. A., Schito, M. L., Fernando, M. A., Martin, A. and Danforth, H. D., *Int. J. Parasitol.* 1998, 28, 485–492.

Eckert, J., Taylor, M., Catchpole, J., Licois, D., Coudert, P. and Bucklar, H., in: Eckert, J., Braun, R., Shirley, M. W. and Coudert, P. (Eds.), *Guidelines on techniques in coccidiosis research*, European Commission, Luxembourg 1995, pp. 103–119.

Ellsworth, D. L., Rittenhouse, K. D. and Honeycutt, R. L., *Biotechniques* 1993, 14, 214–217.

Gasser, R. B., Eckert, J. and Rohrer, L., *Parasitol. Res.* 1987, 74, 103–111.

Gasser, R. B., *Int. J. Parasitol.* 1997, 27, 1449–1463.

Greif, G., Stephan, B. and Haberkorn, A., *Parasitol. Res.* 1996, 82, 706–714.

Johnston, D. A. and Fernando, M. A., *Parasitol. Res.* 1995, 81, 91–97.

Johnston, D. A. and Fernando, M. A., *Parasitol. Res.* 1997, 83, 464–470.

MacPherson, J. M., Eckstein, P. E., Scoles, G. J. and Gajadhar, A. A., *Mol. Cell. Probes* 1993, 7, 293–299.

McDougald, L. R. and Reid, W. M., in: Calnek, B. W., Barnes, H. J., Beard, C. W., McDougald, L. R. and M., S. Y. (Eds.), *Diseases of Poultry*, 10th Edition, Iowa State University Press, Ames, Iowa 1997, pp. 865–883.

Molloy, J. B., Eaves, F. W., Jeston, P. J., Minchin, C. M., Stewart, N. P., Lew, A. E. and Jorgensen, W. K., *Avian Dis.* 1998, 42, 119–123.

Orita M., Suzuki Y, Sekiya T, Hayashi K., *Genomics*, 1989, 5, 874–879.

Sambrook, J., Fritsch, E. F., Maniatis, T., *Molecular cloning: a laboratory manual*, 2nd ed, Cold Spring Harbour Press, 1989

Schnitler, B. E., Thebo, P. L., Mattson, J. G., Tomley, F. M. and Shirley, M. W., *Avian Pathol.* 1998, 27, 490–497.

Schnitzler, B. E., Thebo, P. L., Tomley, F. M., Uggla, A. and Shirley, M. W., *Avian Pathol.* 1999, 28, 89–93.

Shirley, M. W. and Bumstead, N., *Parasitol. Res.* 1994, 80, 346–351.

Shirely, M. W., *Res. Vet. Sci.* 1994, 57, 10–14.

Shirley, M. W., in: Eckert, J., Braun, R., Shirley, M. W. and Coudert, P. (Eds.), *Guidelines on techniques in coccidiosis research*, European Commission, Luxembourg 1995, pp. 1–24.

Stucki, U., Braun, R. and Roditi, I., *Exp. Parasitol.* 1993, 76, 68–75.

Zhu, X. Q. and Gasser, R. B., *Electrophoresis* 1998, 19, 1366–1373.

What is claimed is:

1. A method of identifying Eimeria species in a sample, said method comprising the steps:

providing a sample comprising genomic template DNA to be tested;

providing genomic DNA of one or more Eimeria species standards of known identity;

providing a pair of Eimeria genus-specific PCR primers selected from the group consisting of:
  (a) a pair of PCR primers comprising a primer comprising at least 15 consecutive bases of the DNA sequence WW1 (SEQ ID NO: 31) and a primer comprising at least 15 consecutive bases of the DNA sequence WW3r (SEQ ID NO: 32); and
  (b) a pair of PCR primers comprising a primer comprising at least 15 consecutive bases of the DNA sequence WW2 (SEQ ID NO: 33) and a primer comprising at least 15 consecutive bases of the DNA sequence WW4r (SEQ ID NO: 34);

amplifying by means of PCR using said pair of PCR primers a region of said genomic template DNA to be tested and a region of said genomic DNA of one or more Eimeria species standards, thereby producing one or more PCR products from said sample and one or more PCR products from said one or more Eimeria species standards;

comparing the number and size and/or sequence of said one or more PCR products from said sample with the number and size and/or sequence of said one or more PCR products from said one or more Eimeria species standards, wherein said comparing determines the species of Eimeria present within the sample, thereby identifying Eimeria species present in a sample.

2. A method as claimed in claim 1, wherein said pair of PCR primers comprises a primer comprising the DNA sequence WW1 (SEQ ID NO: 31) and a primer comprising the DNA sequence WW3r (SEQ ID NO: 32).

3. A method as claimed in claim 1, wherein said pair of PCR primers comprises a primer comprising the DNA sequence WW2 (SEQ ID NO: 33) and a primer comprising the DNA sequence WW4r (SEQ ID NO: 34).

4. A method as claimed in claim 1 wherein said amplifying comprises two PCRs, wherein one of said PCRs employs the pair of PCR primers of (a), and wherein the other of said PCRs employs the pair of PCR primers of (b).

5. A method as claimed in claim 1 wherein said amplifying comprises one PCR, wherein the pair of PCR primers of (a) and the pair of PCR primers of (b) are employed together in said one PCR.

6. A method as claimed in claim 1, wherein the number and size and/or sequence of said one or more PCR products is determined by gel electrophoresis.

7. A method as claimed in claim 6, wherein the method of gel electrophoresis is selected from the group consisting of:
   denaturing polyacrylamide gel electrophoresis (DPGE); and
   single-stranded conformation polymorphism (SSCP) analysis.

8. A method as claimed in claim 7, wherein both denaturing polyacrylamide gel electrophoresis (DPGE) and single-stranded conformation polymorphism (SSCP) analysis are employed.

9. The method as claimed in claim 6, wherein said gel electrophoresis is conducted in an automated electrophoretic system.

* * * * *